(12) United States Patent
Kikkawa et al.

(10) Patent No.: US 9,307,933 B2
(45) Date of Patent: Apr. 12, 2016

(54) MICROPORE FORMING APPARATUS AND MICROPORE FORMING METHOD

(75) Inventors: Yasuo Kikkawa, Kakogawa (JP); Toshiyuki Sato, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 393 days.

(21) Appl. No.: 13/161,910

(22) Filed: Jun. 16, 2011

(65) Prior Publication Data
US 2011/0319920 A1 Dec. 29, 2011

(30) Foreign Application Priority Data
Jun. 24, 2010 (JP) .................................. 2010-144089

(51) Int. Cl.
| A61B 17/34 | (2006.01) |
| A61B 5/15 | (2006.01) |
| A61B 5/151 | (2006.01) |
| A61B 5/145 | (2006.01) |

(52) U.S. Cl.
CPC ........... *A61B 5/1411* (2013.01); *A61B 5/14514* (2013.01); *A61B 5/15186* (2013.01)

(58) Field of Classification Search
CPC ............. A61B 5/1411; A61B 5/15186; A61B 5/14514
USPC ............... 606/131, 186, 182; 81/9.22; 604/46
See application file for complete search history.

(56) References Cited

U.S. PATENT DOCUMENTS

| 5,618,295 | A * | 4/1997 | Min ............................. 606/171 |
| 6,689,103 | B1 * | 2/2004 | Palasis ......................... 604/173 |
| 7,131,960 | B2 * | 11/2006 | Trautman et al. ............... 604/46 |
| 7,419,481 | B2 * | 9/2008 | Trautman et al. ............. 604/500 |
| 2002/0032415 | A1 * | 3/2002 | Trautman et al. ............. 604/272 |
| 2002/0087182 | A1 * | 7/2002 | Trautman et al. ............. 606/186 |
| 2002/0091357 | A1 | 7/2002 | Trautman et al. |
| 2004/0064087 | A1 * | 4/2004 | Lastovich et al. ............... 604/46 |
| 2007/0038147 | A1 | 2/2007 | Mechelke et al. |
| 2007/0233011 | A1 | 10/2007 | Hagino et al. |
| 2008/0039775 | A1 * | 2/2008 | Ameri et al. ..................... 604/46 |
| 2009/0137945 | A1 * | 5/2009 | Marquez ......................... 604/46 |
| 2009/0222000 | A1 * | 9/2009 | Pacey .............................. 606/33 |
| 2010/0241151 | A1 * | 9/2010 | Rickard ........................ 606/186 |
| 2011/0124998 | A1 | 5/2011 | Okada |

FOREIGN PATENT DOCUMENTS

| EP | 1 787 584 A1 | 5/2007 |
| EP | 1787584 A1 | 5/2007 |
| EP | 1 834 589 A2 | 9/2007 |
| EP | 1834589 A2 | 9/2007 |
| JP | 2007-44527 | 2/2007 |
| JP | 200744527 | 2/2007 |
| JP | 2009-509679 | 3/2009 |

(Continued)

*Primary Examiner* — Thomas McEvoy
*Assistant Examiner* — Julie A Szpira
(74) *Attorney, Agent, or Firm* — Brinks Gilson & Lione

(57) ABSTRACT

To provide a micropore forming apparatus capable of increasing the amount of interstitial fluid extracted from micropores formed in the skin of a subject. The micropore forming apparatus includes a skin contact part that has a plurality of microneedles for piercing the skin of the subject, and a force exerting part for exerting a force on the skin contact part toward the skin of the subject. The force exerting part is configured so as to exert a force on the microneedles toward the skin at a position at which the microneedles of the skin contact part are to pierce the skin of the subject.

9 Claims, 22 Drawing Sheets

(56) References Cited

FOREIGN PATENT DOCUMENTS

| | | |
|---|---|---|
| JP | 2009209679 | 3/2009 |
| WO | WO 02/30301 A1 | 4/2002 |
| WO | WO02/30301 A1 | 4/2002 |
| WO | WO2004/045375 A2 | 6/2004 |
| WO | WO 2004/045375 A2 | 6/2004 |
| WO | WO 2007/002521 A2 | 1/2007 |
| WO | WO2007/002521 A2 | 1/2007 |
| WO | WO2007/041355 | 4/2007 |
| WO | WO2009/101112 | 8/2009 |
| WO | WO2009/101112 A1 | 8/2009 |
| WO | WO2010/013808 | 2/2010 |
| WO | WO2010/013808 A1 | 2/2010 |

* cited by examiner

MICROPORE FORMING APPARATUS AND MICROPORE FORMING METHOD

RELATED APPLICATIONS

This application claims priority under 35 U.S.C. §119 to Japanese Patent Application No. 2010-144089 filed on Jun. 24, 2010, the entire content of which is hereby incorporated by reference.

BACKGROUND OF THE INVENTION

1. Field of the Invention

The present invention relates to a micropore forming apparatus and micropore forming method for forming micropores in the skin of a subject by piercing the skin with microneedles.

2. Description of the Related Art

There is known art for forming micropores in the skin of a subject by piercing the skin of the subject via a microneedle tip provided with a plurality of microneedles in order to measure a predetermined component, such a glucose, present in the interstitial fluid of the subject (US2007-0233011). In the piercing apparatus used for micropore formation described in US2007-0233011, after the piercing operation has been performed, a measuring device is mounted on the pierced region, interstitial fluid is extracted from the skin, and the glucose content is then measured.

The piercing device disclosed in US2007-0233011 causes a microneedle tip to pierce the skin of the subject to form micropores therein by driving a spring-operated piston (chuck array), the leading end of which is provided with the microneedle tip that has a plurality of microneedles for piercing.

The present applicant has proposed a method for calculating (estimating) the glucose time-area under the curve of a subject using the sodium ion content of the interstitial fluid (US2011-0124998). In this method, interstitial fluid is extracted from the skin by forming micropores in the skin of the subject using a piercing device, and adhering, for a predetermined time (for example, 60 minutes or longer), an interstitial fluid collection sheet comprising a gel collection medium onto the skin where the micropores have been formed. Then, the amounts of glucose and sodium ions contained in the interstitial fluid are measured, and the glucose time-area under the curve for the subject is estimated based on the obtained measurements of glucose and sodium ions. In this case, a small amount of sweat from the skin of the subject is also collected in the collection medium, in addition to the interstitial fluid extracted from the micropores. Since this sweat also contains sodium ions, it is desirable that a large amount of interstitial fluid is extracted from the micropores in order to reduce the influence of the sweat on the measurement.

SUMMARY OF THE INVENTION

The scope of the present invention is defined solely by the appended claims, and is not affected to any degree by the statements within this summary.

The conventional art does not, however, describe the increase in the amount of interstitial fluid extracted from the micropores.

The present inventors have conducted intensive study of the increase in the amount of interstitial fluid extracted from micropores formed by the piercing device. As a result, we have completed the present invention after discovering that the amount of interstitial fluid extracted from the formed micropores is increased by pressing the microneedles into the skin for a predetermined time after the microneedles have pierced the skin, without quickly retracting the microneedles back into the device once the microneedles have pierced the skin of the subject as in the conventional art.

The micropore forming apparatus of the present invention is a micropore forming apparatus for forming micropores in the skin by piercing the skin of a subject with microneedles, comprising a skin contact part that has a plurality of microneedles for piercing the skin of the subject; and a force exerting part for exerting a force on the skin contact part toward the skin of the subject;

wherein the force exerting part is configured so as to exert a force on the microneedles toward the skin at a position at which the microneedles of the skin contact part are to pierce the skin of the subject.

The micropore forming apparatus of the present invention is configured such that the microneedles that have pierced the skin of the subject are pressed toward the skin by the force exerting part. That is, in the present invention, the microneedles are pressed toward the skin of the subject for a predetermined time after piercing the skin, unlike the conventional art in which the microneedles are quickly retracted into the piercing device after the microneedles have once pierced the skin of the subject. Thus, micropores can be formed in the skin by all of the microneedles, thereby increasing the amount of collected interstitial fluid and improving the accuracy of the measurements using the extracted interstitial fluid compared to the conventional art.

The micropore forming method of the present invention is a micropore forming method for forming micropores in the skin of a subject using the micropore forming apparatus, wherein the state of the microneedles being pressed into the skin is maintained for a predetermined time after the microneedles have pierced the skin of the subject.

According to the micropore forming apparatus and the micropore forming method of the present invention, it is possible to increase the amount of interstitial fluid extracted from the micropores formed in the skin of a subject.

DETAILED DESCRIPTION OF THE PREFERRED EMBODIMENTS

The embodiments of the micropore forming apparatus and the micropore forming method of the present invention are described in detail hereinafter with reference to the accompanying drawings.

[General Structure of the Micropore Forming Apparatus]

Figure 1:
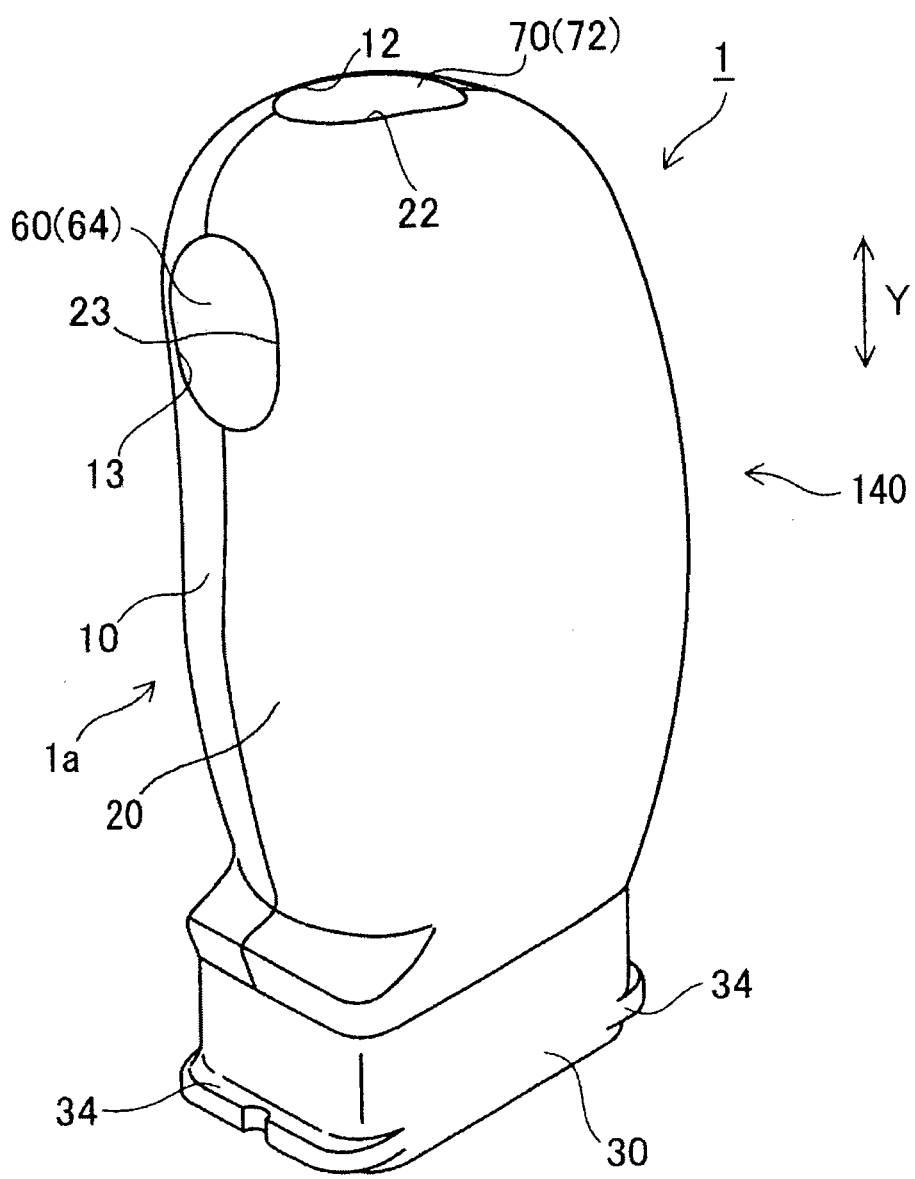
FIG. 1 is a perspective view of the overall structure of an embodiment of the micropore forming apparatus of the present invention.

FIG. 1 is a perspective view showing the overall structure of an embodiment of the micropore forming apparatus 1 of the present invention. FIGS. 2 through 8 illustrate the structural details of each component of the micropore forming apparatus 1 shown in FIG. 1. FIG. 9 is a perspective view of the overall structure of the tip receiver kit provided with a microneedle tip installed in the micropore forming apparatus shown in FIG. 1. FIGS. 10 through 16 illustrate the structural details of each component of the tip receiving kit shown in FIG. 9.

The micropore forming apparatus 1 of the embodiment of the present invention (refer to FIG. 1) is an apparatus for forming fluid extraction holes (micropores) in the skin of a subject by mounting a sterilized microneedle tip 110 (refer to FIG. 11) so that the microneedles 113a of the microneedle tip 110 abut (contact) the skin of the subject. Then, fluid (interstitial fluid) exudes from the extraction holes in the skin of the subject formed by the microneedle tip 110 and micropore forming apparatus 1, and the extracted fluid is collected by an extraction medium which is then measured by a glucose concentration analyzer (not shown in the drawings), and the glucose concentration in the interstitial fluid is calculated, and the AUC is calculated based on this value. The structural details of the embodiment of the micropore forming apparatus 1 of the present invention are described below with reference to FIGS. 1 through 12.

Figure 2:
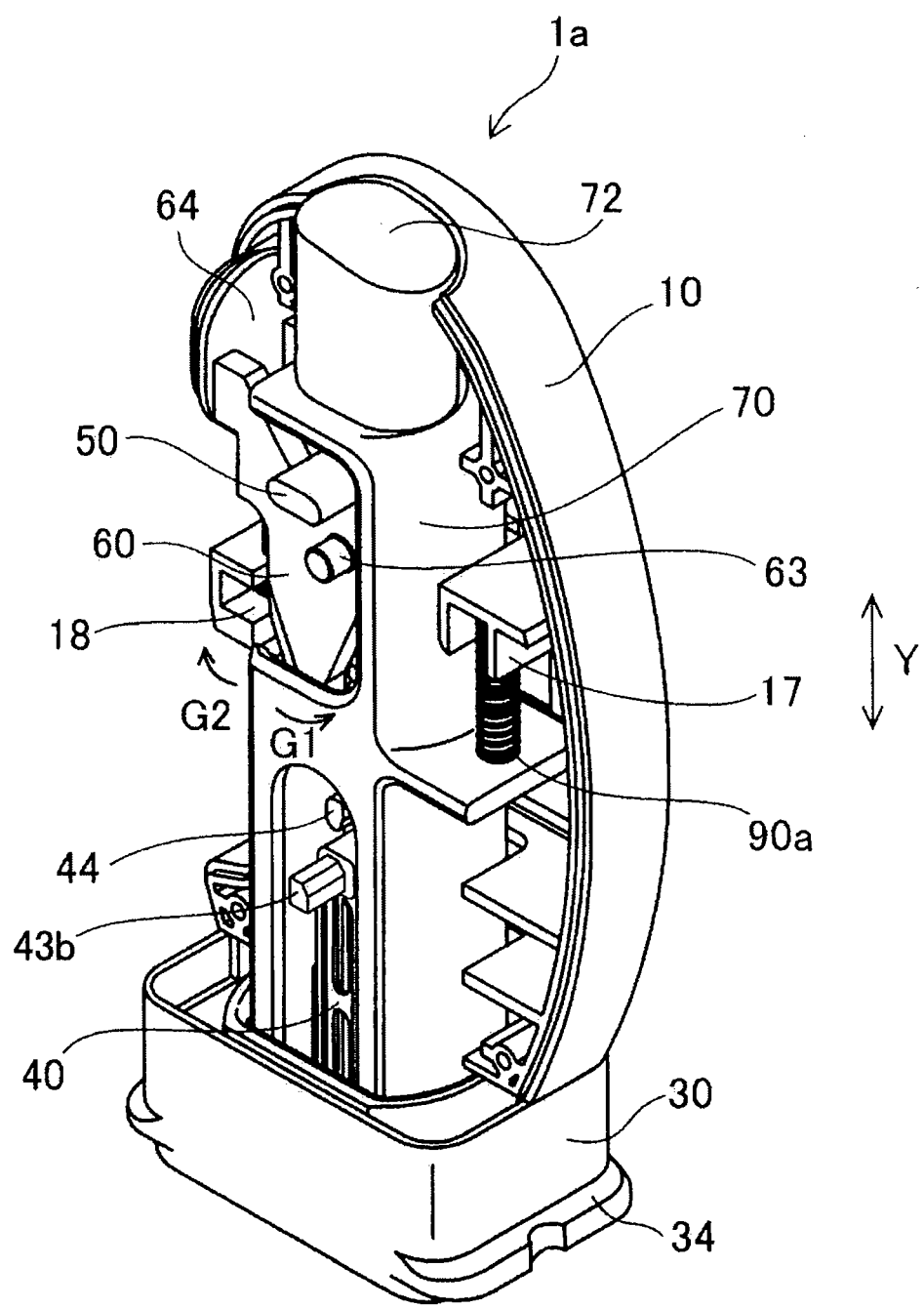
FIG. 2 is a perspective view of the internal structure of the micropore forming apparatus shown in FIG. 1.
Figure 3:
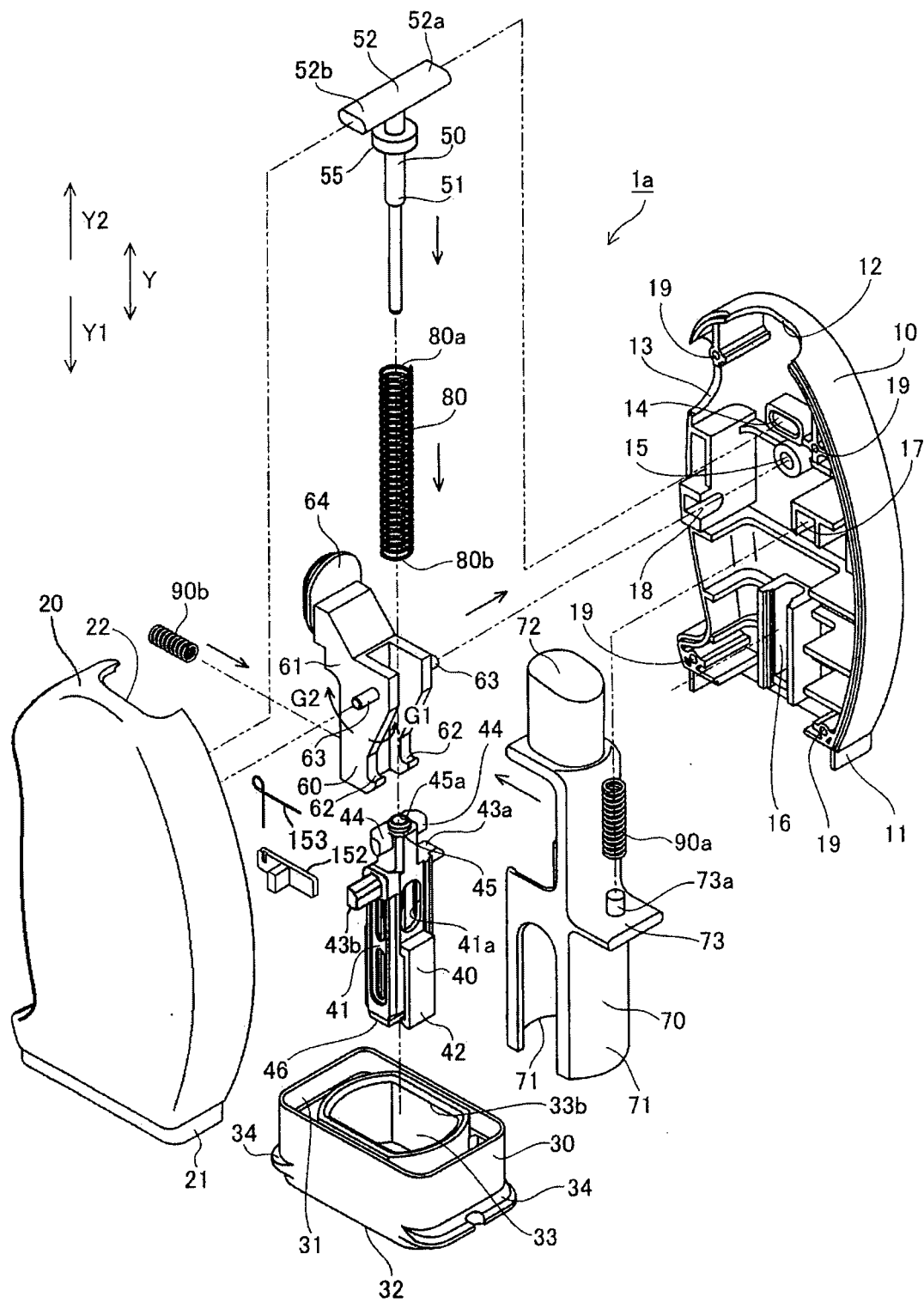
FIG. 3 is an exploded perspective view of the micropore forming apparatus shown in FIG. 1.

The micropore forming apparatus 1 forms a plurality of small extraction holes that pass through the stratum corneum of the epidermis but do not reach so far as the blood vessels in the dermis, thereby inducing exudation of interstitial fluid from the extraction holes. The micropore forming apparatus 1 has a main body unit 1a with a piercing mechanism for piercing the skin of a subject. As shown in FIGS. 1 through 3, the main body unit 1a of the micropore forming apparatus 1 has a rear cover 10, front cover 20, tip receiver insertion member 30, chuck array 40 as a skin contact part, spring stopper 50, release button 60, injector 70, main spring 80 as a force exerting means (refer to FIG. 3), and a plurality of springs 90a and 90b (refer to FIG. 3). Note that the seven members (rear cover 10, front cover 20, tip receiver insertion member 30, chuck array 40, spring stopper 50, release button 60, and injector 70) excluding the springs (main spring 80 and plurality of springs 90a and 90b) are respectively made of synthetic resin. The piercing mechanism of the main body unit 1a of the micropore forming apparatus 1 is mainly configured by the chuck array 40, spring stopper 50, release button 60, and main spring 80.

[Structure of Elements of the Main Body Unit]

Figure 4:
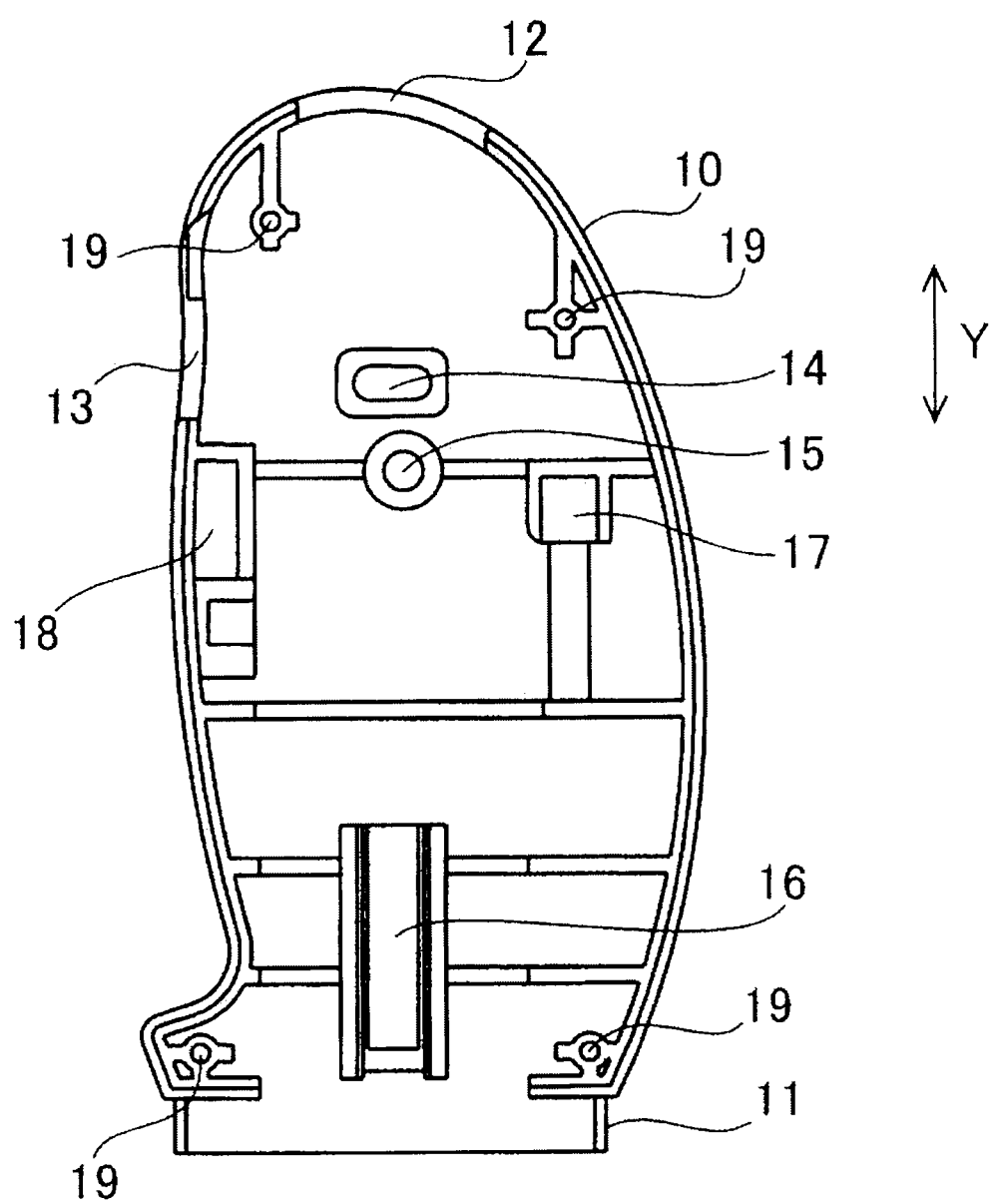
FIG. 4 is a frontal view of the internal structure of the rear cover of the micropore forming apparatus shown in FIG. 1.

As shown in FIGS. 2 and 3, a housing configured by the rear cover 10 and front cover 20 is capable of accommodating therein the chuck array 40, spring stopper 50, release button 60, injector 70, main spring 80, and the plurality of springs 90a and 90b. As shown in FIGS. 3 and 4, a mounting part 11 for mounting the tip receiver insertion member 30 is formed at the bottom part of the rear cover 10. An opening 12 is formed at the top part of the rear cover 10 to expose a button part 72 of the injector 70, and thus to allow a user to press the button part 72. An opening 13 for exposing a button part 64 of the release button 60 is formed on the side surface of the rear cover 10. Within the rear cover 10 are provided a concavity 14 into which is fitted one end part 52a of a spring receiver 52 of the spring stopper 50, a concavity 15 for engaging a support shaft 63 of the release button 60, a guide channel 16 for guiding a guide part 43 of the chuck array 40 which moves in the Y direction (vertical direction in FIGS. 1 through 5) within the housing, spring installation parts 17 and 18 for installing the springs 90a and 90b, and four boss insert holes 19 for inserting the four bosses 27 (refer to FIG. 5) of the front cover 20. Note that, in the present embodiment, one end of the main spring 80 is held within the housing by a spring receiver 52 of the spring stopper 50.

Figure 5:
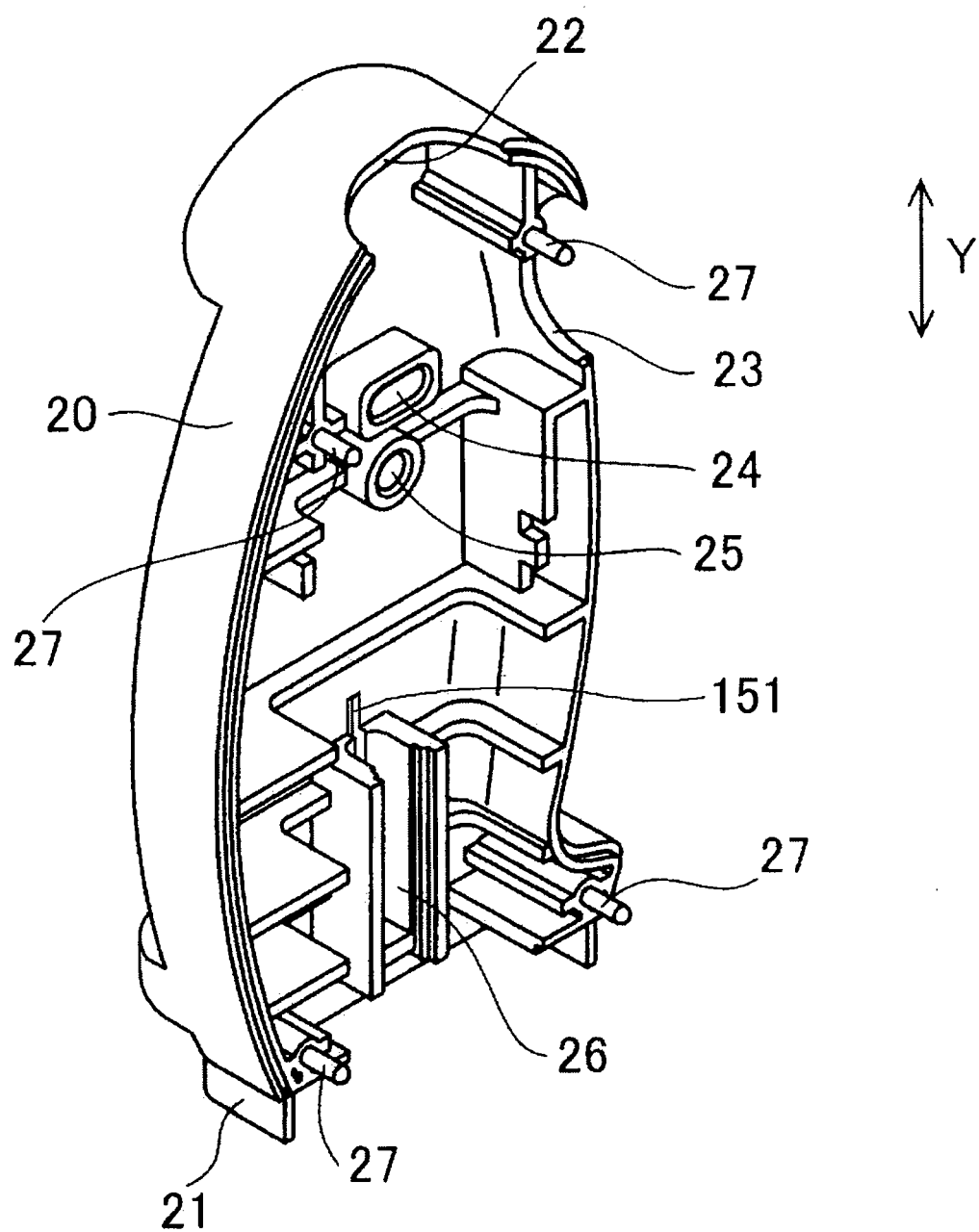
FIG. 5 is a perspective view of the internal structure of the front cover of the micropore forming apparatus shown in FIG. 1.

As shown in FIGS. 3 and 5, the front cover 20, similar to the rear cover 10, has a mounting part 21 for mounting the tip receiver insertion member 30, an opening 22 for exposing the button part 72 of the injector 70 and thus allow a user to press the button part 72, an opening 23 for exposing the button part 64 of the release button 60, a concavity 24 into which is fitted the other end 52b of the spring receiver 52 of the spring stopper 50, a concavity 25 for engaging the support shaft 63 of the release button 60, and a guide channel 26 for guiding the guide part 43 of the chuck array 40 which moves within the housing in the Y direction. Four bosses 27 are formed on the front cover 20 at positions corresponding to the four boss insert holes 19 (refer to FIG. 3) of the rear cover 10. Therefore, the front cover 20 can be positioned and mounted relative to the rear cover 10 by inserting the four bosses 27 of the front cover 20 into the boss insert holes 19 of the rear cover 10.

Figure 6:
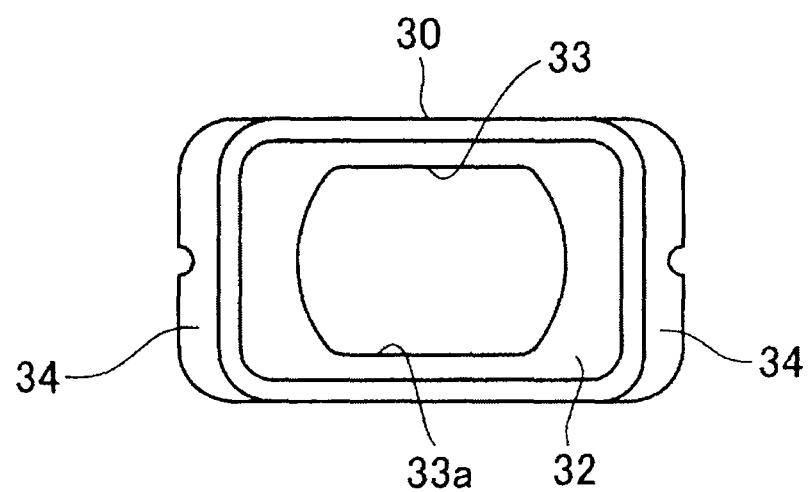
FIG. 6 is a bottom view of the tip insertion member of the micropore forming apparatus shown in FIG. 1.

The tip receiver insertion member 30 is inserted through the tip receiver 120 that accommodates the microneedle tip 110 during installation of the microneedle tip 110 (refer to FIG. 11), and inserted through the empty tip receiver 120 when discarding the used microneedle tip 110. As shown in FIGS. 3 and 6, the tip receiver insertion member 30 includes a mounting part 31 for mounting the mounting part 11 of the rear cover 10 and the mounting part 21 of the front cover 20, a contact surface 32 for contacting the skin on the arm of a subject, a through hole 33 that has an opening 33a (refer to FIG. 6) formed on the contact surface 32 and an opening 33b (refer to FIG. 3) disposed on the opposite side thereof, and two flanges 34 formed so as to extend outward from the outer surface in a lateral direction.

In the present embodiment, the opening 33a formed on the side of the contact surface 32 is configured such that the tip receiver 120 (refer to FIG. 10), which accommodates the removable microneedle tip 110, is insertable therein. The tip receiver 120 passes through the opening 33a and can then travel in the Y direction through the through hole 33.

Figure 7:
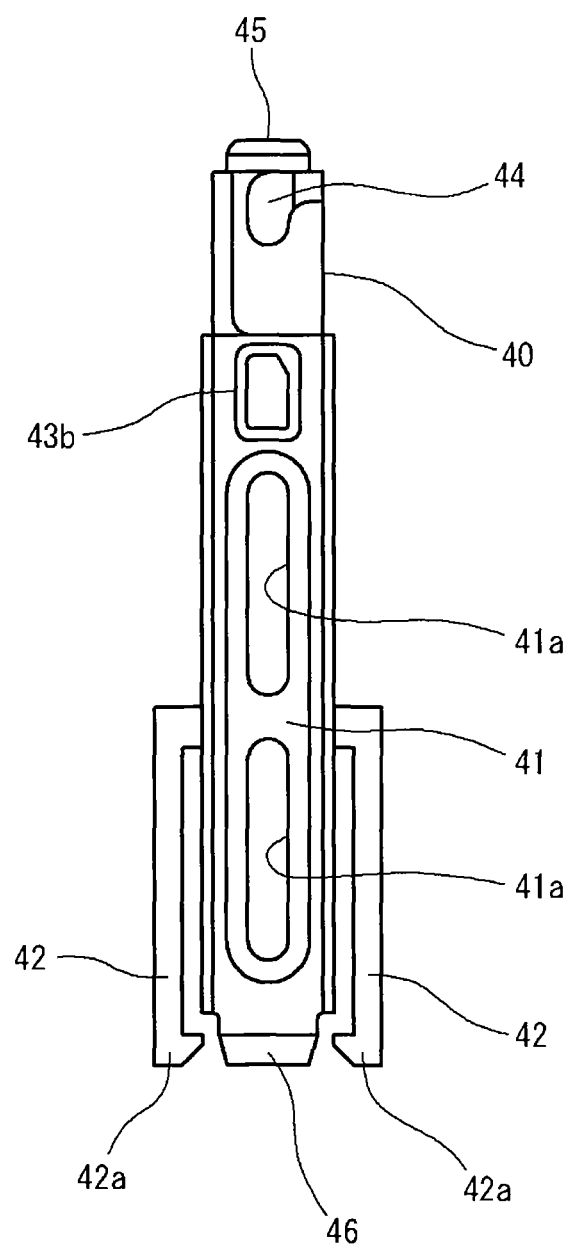
FIG. 7 is a frontal view of the chuck array of the micropore forming apparatus shown in FIG. 1.

The chuck array 40 functions as a piston to cause the microneedle tip 110 to strike or contact the skin of the subject, and is configured to be movable in the Y direction along the guide channel 26 of the front cover 20 and the guide channel 16 of the rear cover 10. The microneedle tip 110 (refer to FIG. 11) being held in the chuck array 40 can travel in the Y direction through the tip receiver insertion member 30. As shown in FIGS. 3 and 7, the chuck array 40 includes a main body 41 provided with a plurality of holes 41a to reduce weight, a pair of elastically deformable chucks 42 for engaging the flanges 112 (refer to FIG. 12) of the microneedle tip 110 so as to hold the microneedle tip 110, a guide part 43a to be inserted into the guide channel 16 of the rear cover 10, and a guide part 43b to be inserted into the guide channel 26 of the front cover 20, two connection parts 44 for engaging the two fixed parts 62 of the release button 60 (to be described later), a convexity 45 having an insertion hole 45a (refer to FIG. 3 for inserting a shaft 51 of the spring stopper 50 (to be described later), and a bushing part 46 formed on the bottom side (side in the arrow Y1 direction) of the main body 41. The leading end 42a of the chucks 42 that abut the flange 112 of the microneedle tip 110 are tapered and have a hook shape allowing engagement with the flange 112.

In the present embodiment, when the two connection parts 44 do not engage the two fixed parts 62 of the release button 60 (to be described later), the chuck array 40 automatically holds the microneedle tip 110 accommodated within the tip receiver 120 by inserting the microneedle 110 (refer to FIG. 10) into the opening 33a of the tip receiver insertion member 30. Then, the chuck array 40, which is movable in the Y direction, holds the microneedle tip 110, and thereafter moves to the arrow Y2 direction until the connection parts 44 are locked to the fixed parts 62.

Also in the present embodiment, when the two connection parts 44 do not engage the two fixed parts 62 of the release button 60 (to be described later), the microneedle tip 110 held by the chuck array 40 automatically removes the tip receiver 120 from the chucks 42 of the chuck array 40 by inserting the tip receiver 120 into the opening 33a of the tip receiver insertion member 30.

In the present embodiment, the chucks 42 are integratedly formed of synthetic resin together with the other parts (main body 41, guide parts 43a and 43b, connection parts 44, convexity 45, and bushing part 46).

The spring stopper 50 is provided to support the main spring 80 which exerts a force on the chuck array 40 in the arrow Y1 direction. As shown in FIG. 3, the spring stopper 50 includes a shaft 51 to be inserted within the main spring 80, and a spring receiver 52 for preventing the main spring 80 from escaping upward (arrow Y2 direction) when the shaft 51 is inserted in the main spring 80. The leading end part 52a and the other end part 52b of the spring receiver 52 are respectively fitted in the concavity 14 of the rear cover 10 and the concavity 24 (refer to FIG. 5) of the front cover 20. In the present embodiment, a short cylindrical shaped spacer 55 is provided to adjust the compression distance of the main spring 80 to the base of the shaft 51. One end 80a of the main spring 80 (to be described later) abuts the bottom surface of the spacer 55. The length of the spacer 55 in the axial direction is suitably variable in accordance to the desired compression distance of the main spring 80. The spacer 55 can be omitted by adjusting the spring constant and length of the main spring 80.

Figure 8:
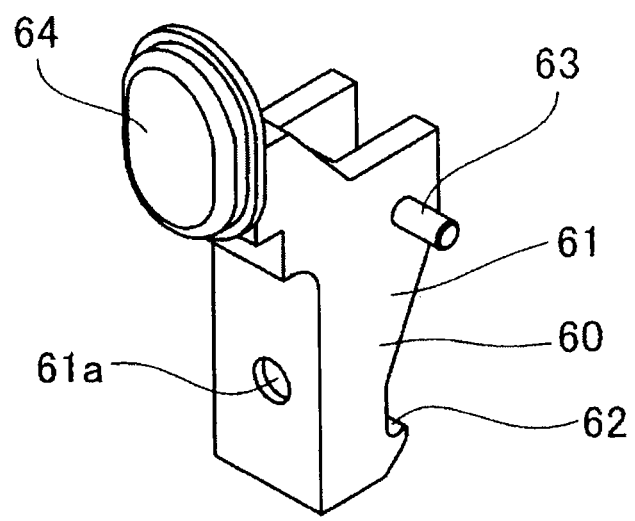
FIG. 8 is a perspective view of the release button of the micropore forming apparatus shown in FIG. 1.
Figure 9:
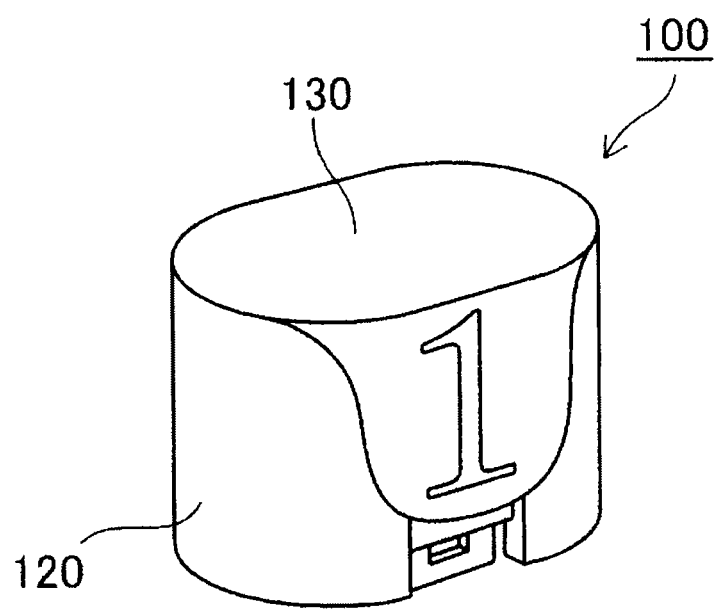
FIG. 9 is a perspective view of the overall structure of the tip receiver kit provided with a microneedle tip installed in the micropore forming apparatus shown in FIG. 1.

As shown in FIGS. 3 and 8, the rear cover 10 is provided with a main body 61, two fixed parts 62 that engage the two connection parts 44 of the chuck array 40, two support shafts 63 for engaging the concavity 15 of the rear cover 10 and the concavity 25 (refer to FIG. 5) of the front cover 20, and a button part 64 that is exposed from the opening 13 in the side surface of the rear cover 10 and the opening 23 (refer to FIG. 5) in the side surface of the front cover 20. As shown in FIG. 8, the side surface of main body 61 that has the button part 64 is also provided with a concavity 61a accommodates one end of the spring 90b (refer to FIG. 3) installed in the spring installation part 18 (refer to FIGS. 3 and 4) of the rear cover 10. In the present embodiment, the two fixed parts 62 function as stoppers that fix the chuck array 40 moving in the arrow Y2 direction against the force of the main spring 80 (to be described later) exerted in the arrow Y1 direction, and maintain the chuck array 40 at the firing standby position.

In this embodiment, the ejector 70 has the function of discharging the tip receiver 120 that accommodates the microneedle tip 110 from the through hole 33 (refer to FIG. 3) of the tip receiver insertion member 30. As shown in FIG. 3, the injector 70 is provided with a pressing part 71 for pressing the edge part 121b (refer to FIG. 10) and edge part 122d (refer to FIG. 14) of the tip receiver 120 (to be described later), a button part 72 that is exposed from the opening 12 of the rear cover 10 and the opening 22 of the front cover 20 so as to be pressable by the user, and a contact part 73 that contacts one end of the spring 90a installed in the spring installation part 17 of the rear cover 10. A boss part 73a to be inserted into the interior of the spring 90a is formed on the contact part 73 to prevent the spring 90a from being removed from the spring installation part 17 of the rear cover 10.

The main spring 80 is provided to exert a force on the chuck array 40 in the arrow Y1 direction. As shown in FIG. 3, the shaft part 51 of the spring stopper 50 is inserted into the interior of the main spring 80. In this case, one end part 80a of the main spring 80 contact the spacer 55, and the spacer 55 contact the spring receiver 52 of the spring stopper 50. The other end part 80b of the main spring 80 contacts the top surface of the connection part 44 of the chuck array 40. That is, the main spring 80, which is a force exerting means in the present embodiment, is in a free state and neither end is fixedly attached to any other member.

When the spring 90a is installed in the spring installation part 17 of the rear cover 10 and the boss part 73a of the contact part 73 of the injector 70 is inserted in the spring 90a, the spring 90a functions to exert a force on the injector 70 in the arrow Y1 direction when the injector 70 is pushed in the arrow Y2 direction, as shown in FIG. 3. When the spring 90b is installed in the spring installation part 18 of the rear cover 10 and disposed in the concavity 61a (refer to FIG. 8) of the release button 60, the spring 90b causes the release button 60, which has pivoted on the support shaft 63 in the arrow G2 direction, to then rotate in the arrow G1 direction.

[Tip Receiver Kit]

The tip receiver kit 100, which is configured by the microneedle tip 110 installed in the chuck array 40, the tip receiver 120 that accommodates the microneedle tip 110, and the sterilization seal 130, of the micropore forming apparatus 1 of the present embodiment is described below in detail with reference to FIGS. 1, 3, 7, and 9 through 16.

Figure 10:
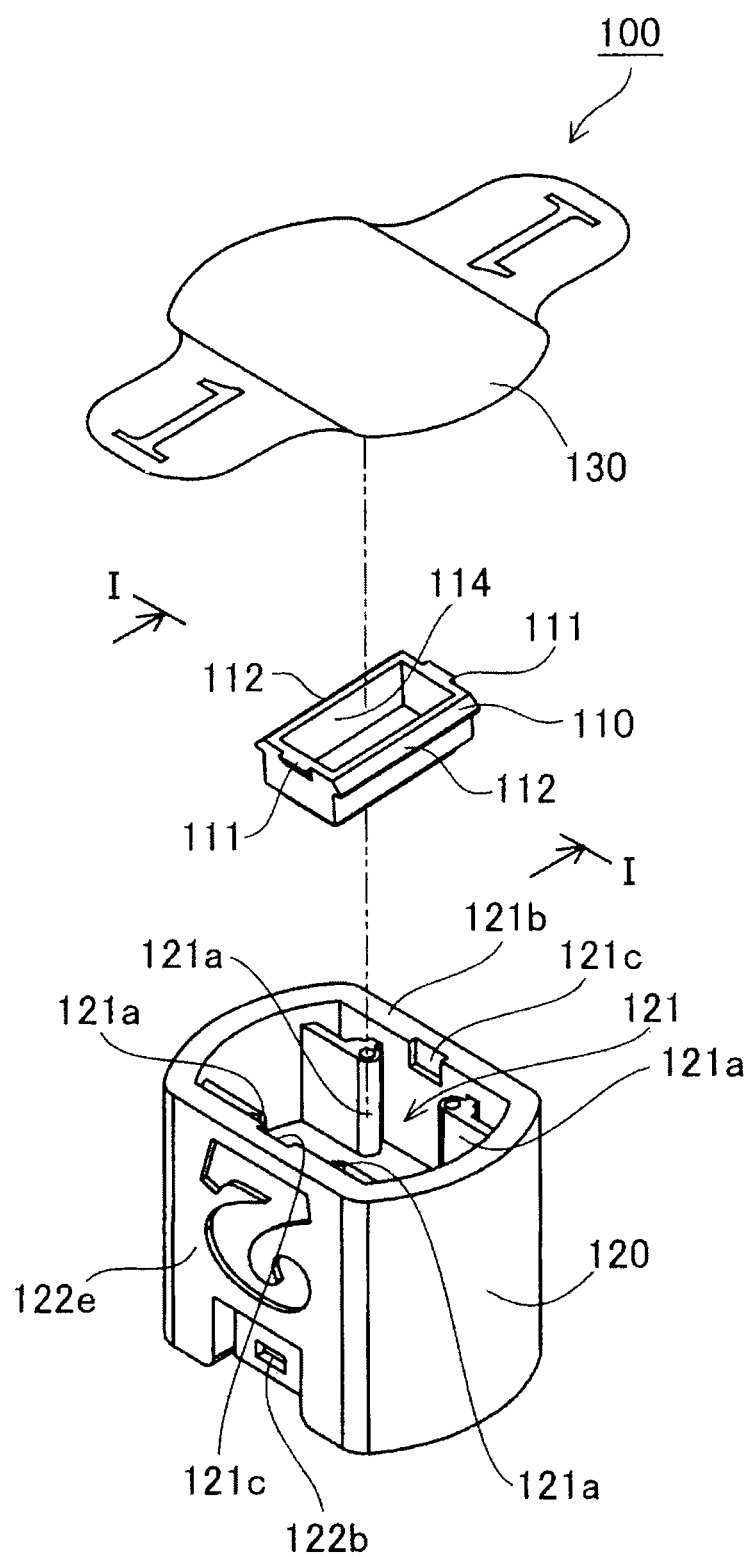
FIG. 10 is an exploded perspective view of the tip receiver kit shown in FIG. 9.
Figure 11:
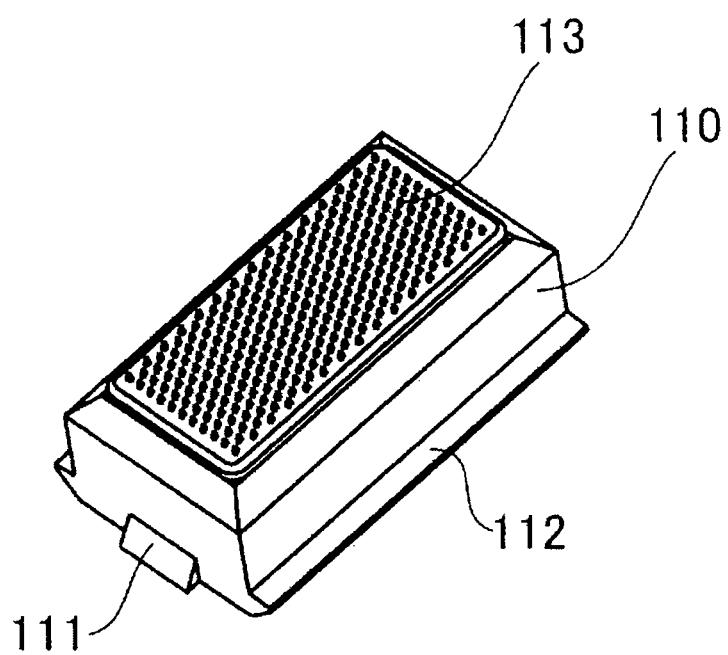
FIG. 11 is a perspective view of the microneedle tip of the tip receiver kit shown in FIG. 9.
Figure 12:
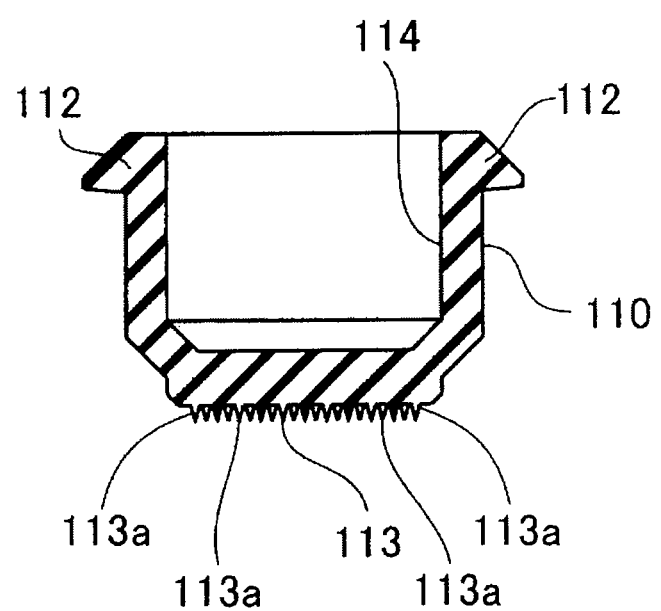
FIG. 12 is a cross sectional view on the I-I line of FIG. 10.

The microneedle tip 110 is used when installed in the array chuck 40 (refer to FIG. 7) of the previously described micropore forming apparatus 1, and has a plurality of microneedles 113a for forming micropores to extract interstitial fluid (fluid) from the skin of a subject. As shown in FIGS. 10 through 12, the microneedle tip 110 has a rectangular shape when viewed from the planar aspect, and includes a pair of protrusions 111 disposed so as to protrude to the outside from the exterior surface in a lateral direction, a pair of flanges 112 disposed so as to protrude to the outside from the exterior surface in a longitudinal direction, a microneedle array 113 that has 305 microneedles 113a, and a concavity 114 into which is inserted the bushing part 46 (refer to FIG. 7) of the chuck array 40 of the previously described micropore forming apparatus 1. The pair of protrusions 111 are formed to lock to the locking holes 122b of the tip receiver 120 (to be described later), and the pair of flanges 112 are formed to engage the leading end part 42a of the chuck 42 of the chuck array 40 (refer to FIG. 7). Note that the microneedle tip 110 is made of synthetic resin and incorporates the 305 microneedles 113a. The microneedles 113a of the present embodiment have a conical shape with an apex angle of approximately 30 degrees, as shown in FIG. 12. Note that a microneedle tip that incorporates a microneedle array portion with 189 microneedles may also be used instead of the microneedle tip 110 that incorporates the microneedle array 113 with the previously mentioned 305 microneedles 113a.

Figure 13:
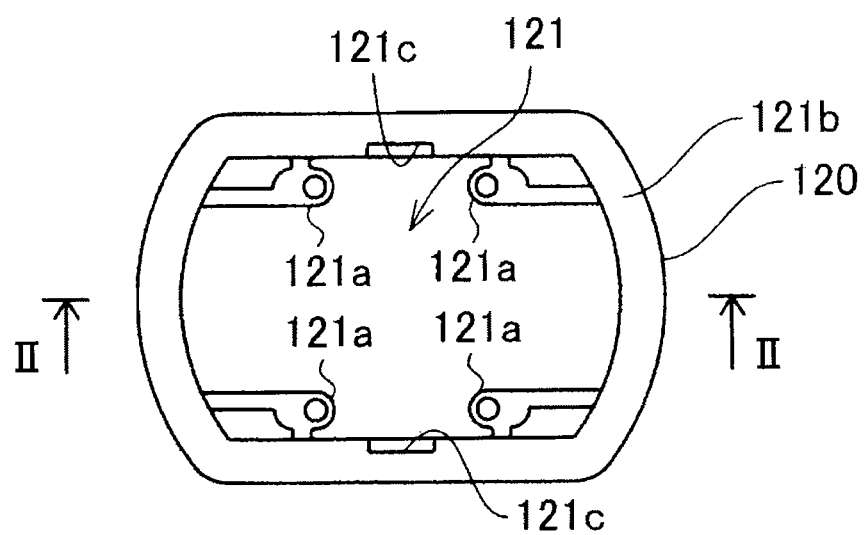
FIG. 13 is a top view of the microneedle tip of the tip receiving member of the tip receiver kit shown in FIG. 9.

In the present embodiment, the synthetic resin tip receiver 120 includes the opening 121 for receiving the sterile and unused microneedle tip 110 (refer to FIG. 10), and the opening 122 for receiving the used microneedle tip 110 that has been used to pierce the skin of a user, as shown in FIGS. 10 and 13 through 16. The opening 121 and the opening 122 are provided on mutually opposite sides, and the sterilization seal 130 (to be described later) is adhered to the opening 121 that accommodates the unused microneedle tip 110 in order to seal the opening 121. As shown in FIGS. 10 and 13, the opening 121 has four supports 121a for supporting the side surface of the sterile and unused microneedle tip 110, an edge part 121b for contacting the pressing part 71 (refer to FIG. 3) of the injector 70, and a clearance part 121c provided so that the protrusion 111 (refer to FIGS. 10 and 11) of the microneedle tip 110 held by the support part 121a does not touch the edge part 121b.

Figure 14:
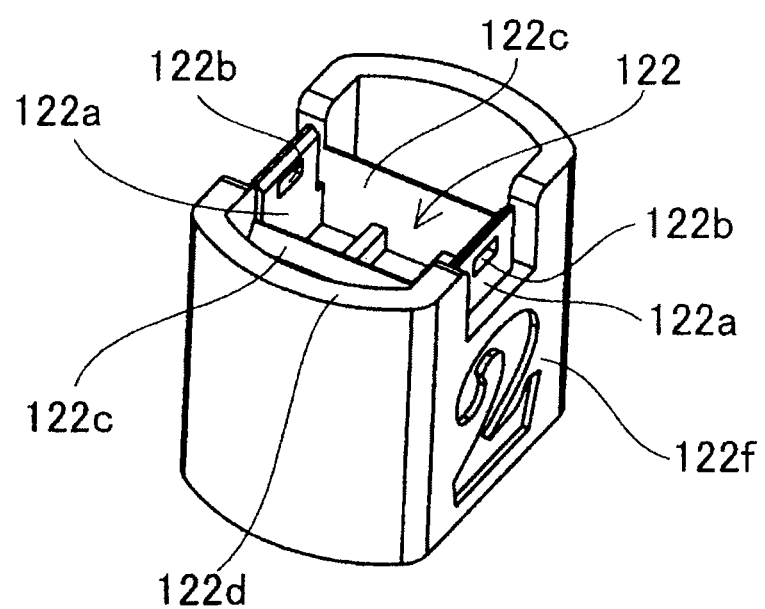
FIG. 14 is a perspective view of the tip receiving member of the tip receiver kit shown in FIG. 9.
Figure 15:
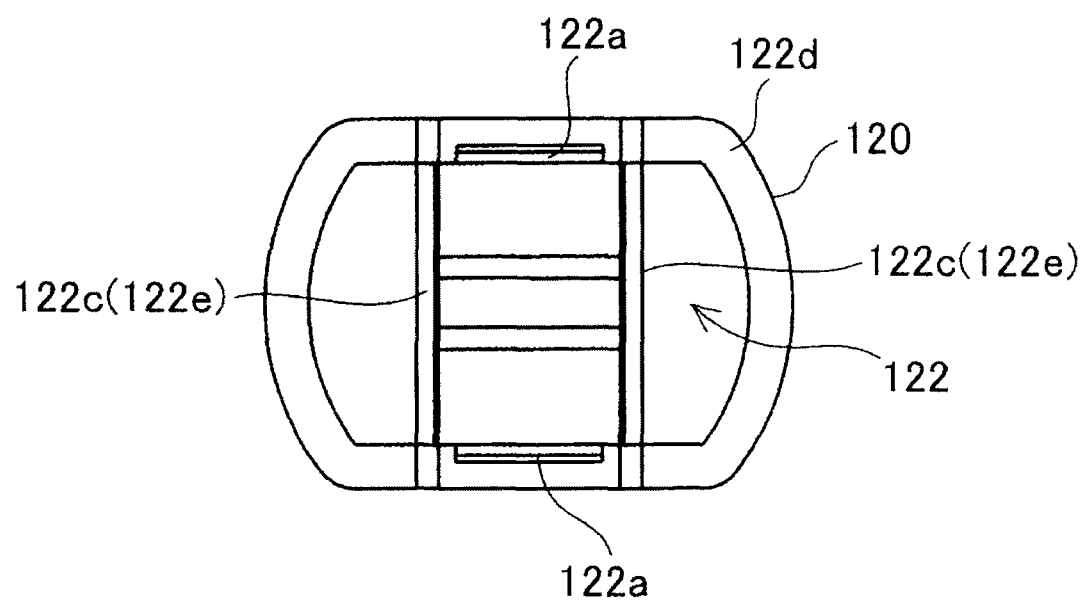
FIG. 15 is a bottom view of the tip receiving member of the tip receiver kit shown in FIG. 9.
Figure 16:
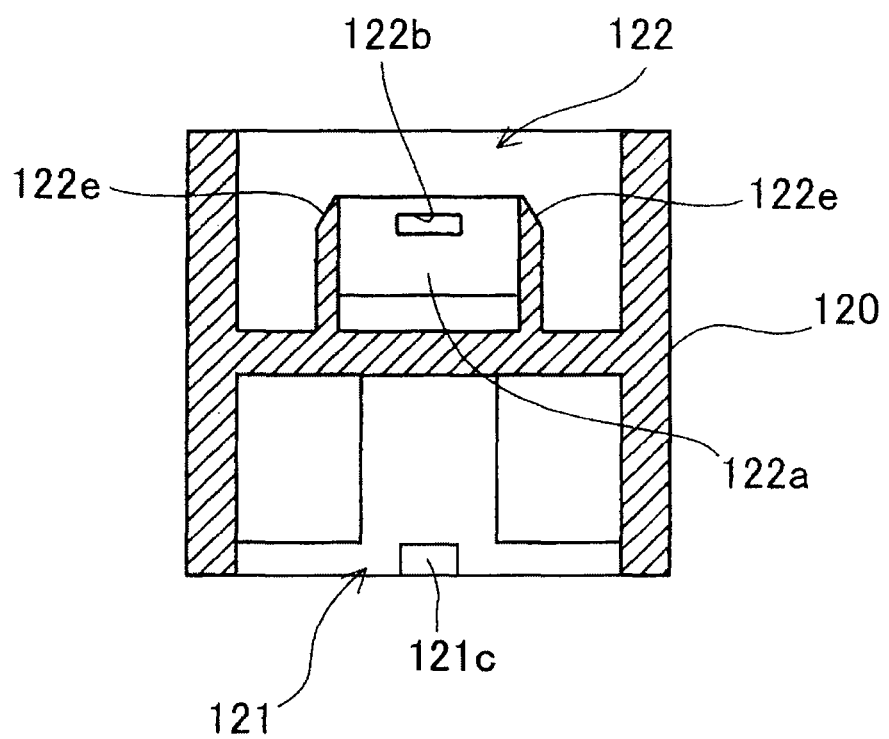
FIG. 16 is a cross sectional view on the II-II line of FIG. 13.

In the present embodiment, the opening 122 includes a holder 122a that has a locking hole 122b into which is inserted the protrusion 111 (refer to FIGS. 10 and 11) of the used microneedle tip 110 that has pierced the skin of the user, as shown in FIGS. 14 and 15. The opening 122 is provided with a release part 122c for releasing the locked state of the flange 112 of the microneedle tip 110 and the chuck 42 (refer to FIG. 7) of the chuck array 40 of the micropore forming apparatus 1, and the edge part 122d that contacts the pressing part 71 (refer to FIG. 3) of the injector 70. The leading end part 122e of the release part 122c has a tapered shape, as shown in FIG. 16. As shown in FIG. 14, the symbol [2] is printed on the side surface 122f of the tip receiver 120 to allow confirmation that the opening 122 is on the top side.

The sterilization seal 130 is made of aluminum film, and functions to prevent viruses and bacteria from adhering to the microneedle tip 110 which has been sterilized by gamma ray exposure or the like. As shown in FIGS. 9 and 10, the sterilization seal 130 is adhered so as to cover the opening 121 that accommodates the unused microneedle tip 110. The sterilization seal 130 is also adhered so as to cover the symbol [2] printed on the side surface 122f of the tip receiver 120 as previously mentioned. As shown in FIG. 9, a symbol [1] is printed on the part of the seal adhered to the side surface 122f of the tip receiver 120 so as to allow confirmation that the opening 121 is disposed on the top side.

In the present embodiment, when the locked state between the connection part 44 of the chuck array 40 and the fixed part 62 of the release button 60 is released, the flange 112 of the microneedle tip 110 is held by the chuck 42 of the chuck array 40 by the subject simply moving the micropore forming apparatus 1 so that the tip receiver 120 is inserted into the opening 33a of the tip receiver insertion member 30 by providing the chuck array 40 to hold the microneedle tip 110 when the tip receiver 120 is inserted into the opening 33a of the tip receiver insertion member 30. At this time, the chuck array 40 can be fixedly anchored by the fixed part 62 in the state of having moved in the Y2 direction against force exerted by the main spring 80 on the chuck array 40 at the same time the microneedle tip 110 is held by the chuck array 40 by configuring the chuck array 40 so as to be movable in the Y direction and by providing the fixed part 62 (release button 60) for engaging the connection part 44 of the chuck array 40 so as to fixedly secure the chuck array 40. Thus, the subject can place the micropore forming apparatus 1 with the chuck array 40 held by the microneedle tip 110 while in a state of being forced in the direction toward the skin (arrow Y2 direction) of the subject. The subject can therefore place the micropore forming apparatus 1 when the apparatus 1 is in a stead of being ready to form micropores in the skin of the subject without requiring complex operation by simply moving the micropore forming apparatus 1. In this state, micropores can be formed in the piercing region of the skin of the subject by pressing the button part 66 of the release button 60 to release the engagement between the connection part 44 of the chuck array 40 and the fixed part 62 so as to move the microneedle tip 110 in the arrow Y1 direction through the opening 33a of the tip receiver insertion member 30.

In the present embodiment, when the microneedle tip 110 is held in the chuck array 40 and the engagement is released between the fixed part 62 and the connection part 44 of the chuck array 40, the used microneedle tip 110 held in the chuck array 40 can be easily removed when the connection with the fixed part 62 has been released by the subject simply moving the micropore forming apparatus 1 so that the tip receiver 120 is inserted into the opening 33a of the tip receiver insertion member 30 by inserting the empty tip receiver that does not accommodate a microneedle tip 110 into the opening 33a of the tip receiver insertion member 30. As a result, the subject can safely discard the used microneedle tip 110 without touching the used microneedle tip 110.

[Pressing the Microneedles into the Skin after Piercing]

In the present embodiment, when the microneedles 113a of the microneedle tip 110 have pierced the skin f the subject via the force exerted by the main spring 80, the microneedles 113a are maintained in the state of piercing the skin and continue to be pressed to the skin of the subject by the force exerted by the main spring 80. Thus, the amount of interstitial fluid extracted from the micropores is increased and the accuracy of the measurement using the extracted interstitial fluid is improved. The pressing condition that is applied in the pierced state, a feature of the present invention, is described below.

Figure 17:
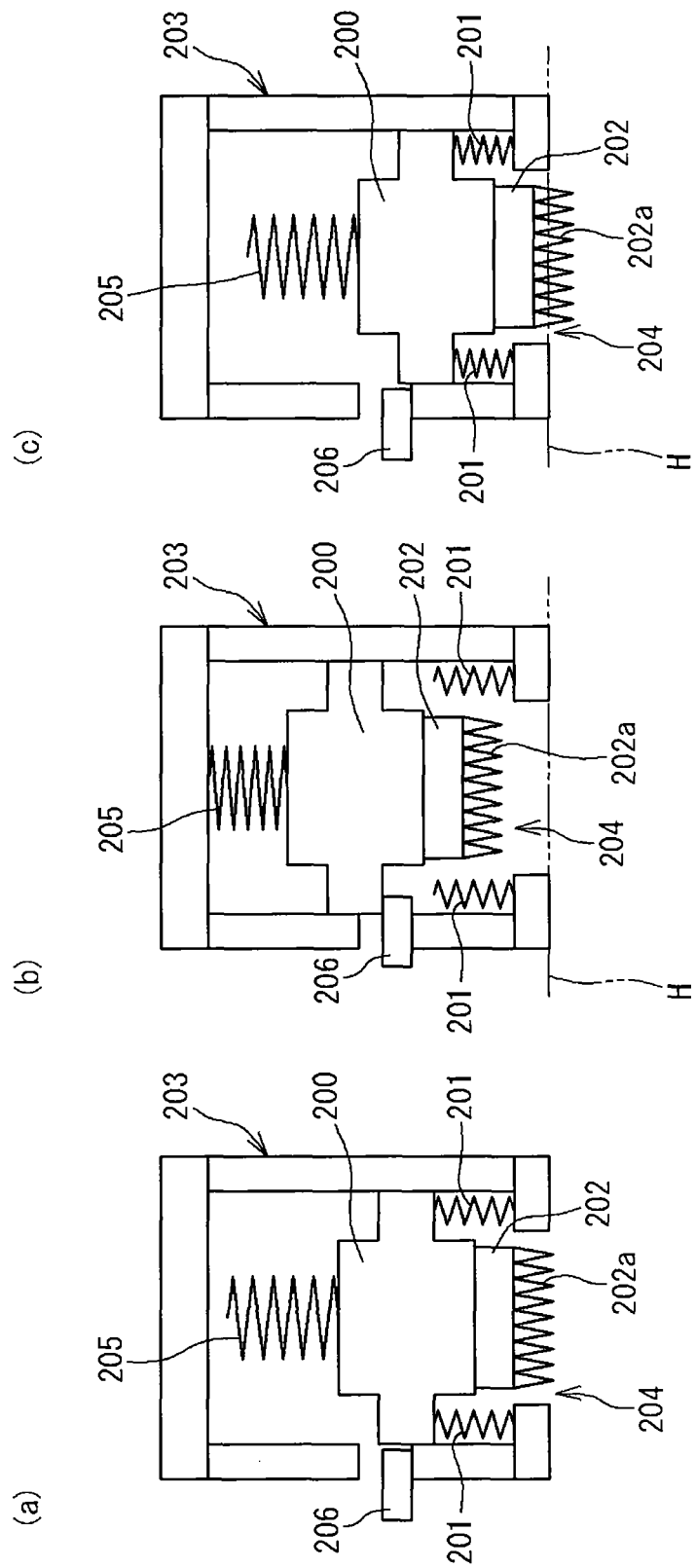
FIGS. 17(a)-17(c) illustrate the launching principle of a conventional micropore forming apparatus.
Figure 18:
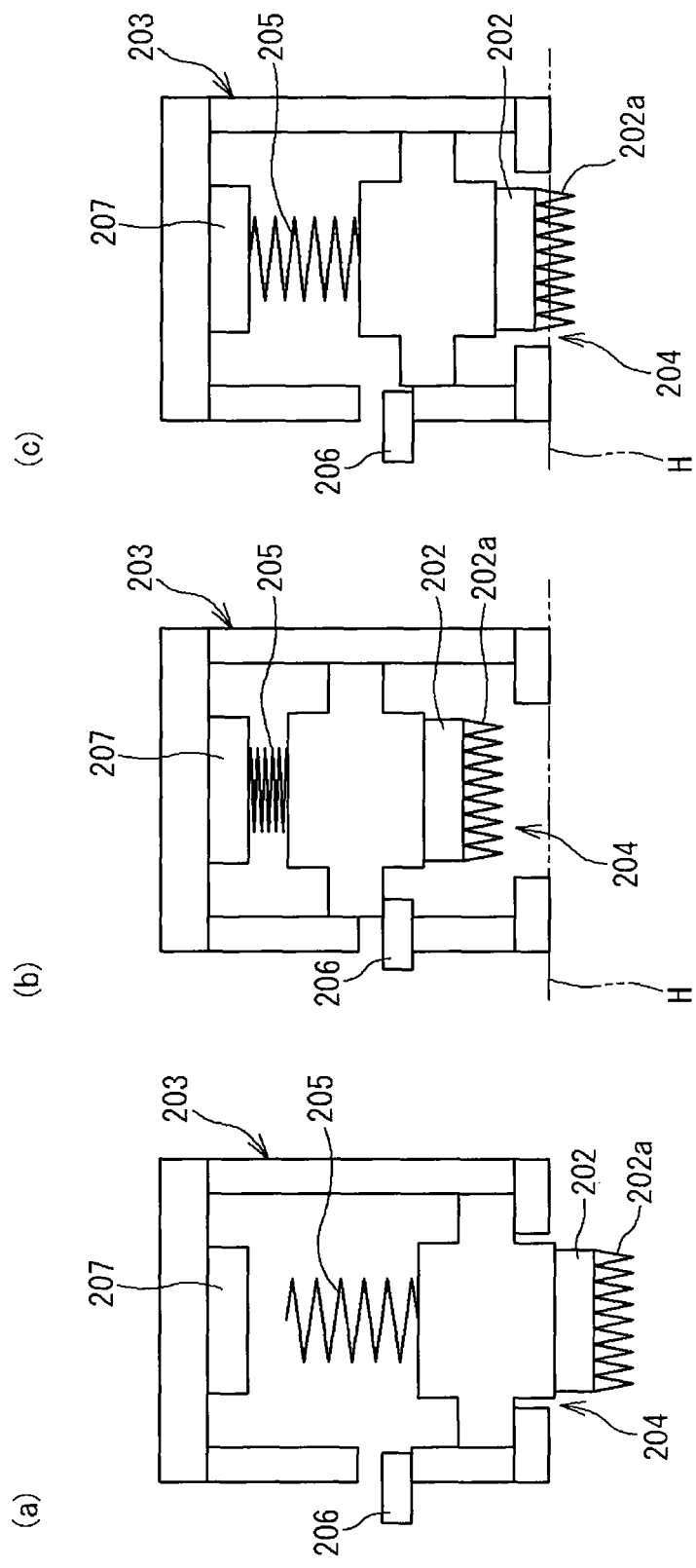
FIGS. 18(a)-18(c) illustrate the launching principle of the micropore forming apparatus of the present invention.

FIG. 17 illustrates the principle of conventional piercing, and shows the principle of conventional piercing in which the microneedles pierce the skin and are then removed from the skin of the subject. FIG. 18 illustrates the principle of piercing in the present invention, and shows the microneedles piercing the skin of the subject and being maintained in that state for a predetermined time during which pressure is applied. Note that only the elements involved in the operation are described and unnecessary elements are omitted from the description to facilitate understanding.

FIG. 17(a) shows the normal state of a conventional micropore forming apparatus; a piston 200 is supported by a spring 201 used to draw the piston 200, and the leading end of the microneedles 202a of a microneedle tip 202 installed in the leading end of the piston 200 are discharged slightly from an opening 204 of a housing 203. A microneedle discharging spring 205 is in an uncompressed state at its full natural length, and there is no force being exerted on the microneedles 202a by the microneedle discharging spring 205 in the direction toward the skin.

FIG. 17(b) shows the loaded state with the piston 200, moved from the state shown in FIG. 17(a) in the non-piercing direction (the opposite direction to the piercing direction, that is, upward in the drawing) with the microneedle discharging piston 205 compressed and maintained thusly by the stopper 206. The piston 200 is separated from the microneedle drawing spring 201, and the microneedles 202a are completely accommodated within the housing 203. In this state, the discharge preparation of the piston 200 is completed when the opening 204 of the housing 203 contact the skin H of the subject.

FIG. 17(c) shows the state wherein the stopper 206 is released from the state shown in FIG. 17(b), and the microneedles 202a have been discharged in the direction toward the skin by the force exerted by the microneedle discharging spring 205. After the microneedles 202a have pierced the skin H of the subject, the microneedles 202a are instantly retracted from the skin H via the force from the skin H and the repulsive force of the microneedle drawing spring 201 that was compressed by the piston 200 when moving in the direction toward the skin.

FIG. 18(a) shows the normal state of the micropore forming apparatus of the present invention; although most of the leading end of the microneedles 202a are discharged from the opening 204 of the housing 203, the microneedle discharging spring 205 is in an uncompressed state at its full natural length and the microneedle discharging spring 205 does not exert a force on the microneedles 202a in the direction toward the skin. Note that in FIG. 18(a) 207 refers to a short cylindrical spacer for adjusting the compression distance of the microneedle discharging spring 205 (corresponding to reference number 55 in FIG. 3), which is provided on the inner side of the housing 203.

FIG. 18(b) shows the loaded state with the piston 200, moved from the state shown in FIG. 18(a) in the non-piercing direction with the microneedle discharging spring 206 compressed and maintained thusly by the stopper 206. In this case, the microneedles 202a are completely accommodated within the housing 203. In this state, the discharge preparation of the piston 200 is completed when the opening 204 of the housing 203 contact the skin H of the subject.

FIG. 18(c) shows the state wherein the stopper 206 is released from the state shown in FIG. 18(b), and the microneedles 202a have been discharged in the direction toward the skin by the force exerted by the microneedle discharging spring 205. When the microneedles 202a are in the state of having pierced the skin H of the subject, the microneedle discharging spring 205 continues to exert a force that presses the microneedles 202a toward the skin. That is, the length, spring constant, and compression distance of the microneedle discharging spring 205 are selected so as to provide this force using the previously mentioned spacer 207 as desired. After the microneedles 202a have pierced the skin H f the subject, the microneedles 202a are still pressed to the skin H by the force exerted microneedle discharging spring 205 that is in excess of the force from the skin H.

[Effectiveness of Pressing after Piercing]

The effectiveness in increasing the amount of extracted interstitial fluid by pressing the microneedles into the skin after piercing was verified by experiment. After the microneedles pierced the skin of the subject, the microneedles were pressed for 5 seconds, 10 seconds, and seconds, then the glucose (Glc) transmittance was measured. The glucose transmittance is an indicator of the amount of glucose extracted to the extraction medium per unit time (glucose extraction time: ng/min) standardized as a glucose value mg/dl. The method of measuring glucose transmittance employs a resin chamber of 90 µL capacity, and filled with RO water (deionized water) as the extraction medium, disposed at the area in which micropores have been formed and through which interstitial fluid passes to the epidermis of the forearm, such that the interstitial fluid is extracted to the chamber. Sampling was performed at 10 minute intervals for 30 minutes. Then, 120 µL of RO water (deionized water) was added to the 90 µL of sampled extraction medium to produce a measurement sample, and the glucose concentration in the measurement sample was analyzed by a fluorescence method using an enzyme. Fluorescence was measured using a microplate reader (MTP-800AFC; Corona Electric Co.) and glucose oxidase (Oriental Yeast Co.), ascorbic acid oxidase (Wako Pure Chemical Industries, Inc.), Amplex Red (Molecular Probes, Inc.), mutarotase (Oriental Yeast Co.), and Peroxidase (Wako Pure chemical Industries, Inc.) as reaction reagents. The glucose value was also measured using a glucose auto analyzer and blood collected from the forearm.

Figure 19:
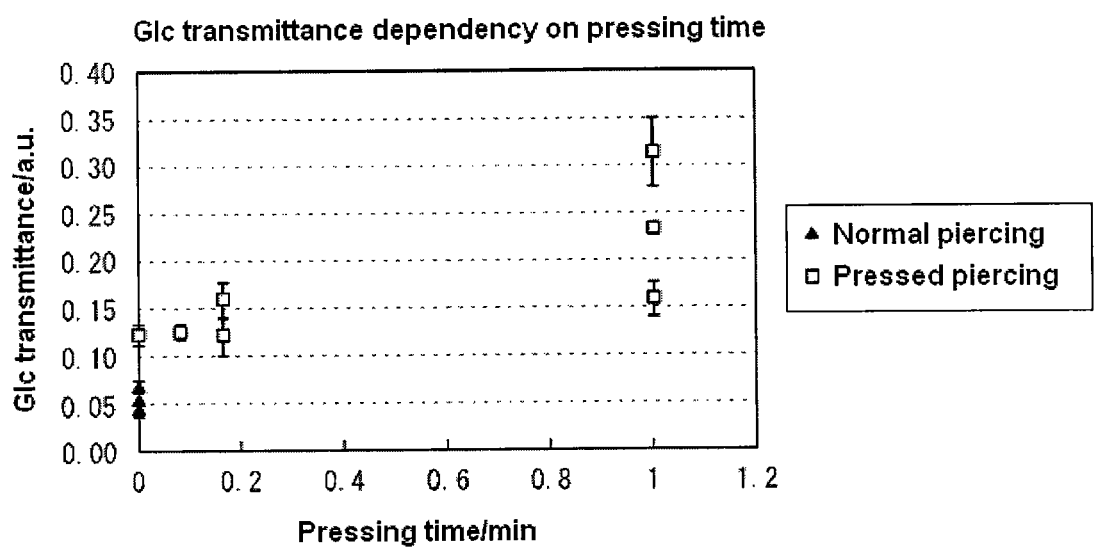
FIG. 19 shows the pressing time dependence of the glucose transmittance.

Glucose transmittance was also measured by a conventional method (microneedles withdrawn from the skin immediately after piercing) for comparison. the results are shown in FIG. 19. In FIG. 19, the box (□) symbol represents extraction with pressing after piercing (method of the present invention), and the triangle (▲) symbol represents extraction by the conventional method (normal piercing). Note that although the box (□) symbol is plotted by the method of the present invention near the zero position of the pressing time, this position represents the bodily sensation pressing time of zero seconds (that is, when the micropore forming apparatus is removed from the skin immediately after the subject feels the piercing of the skin by the microneedles after the start of the piercing operation; the bodily sensation pressing time of the subject is effectively zero seconds although normally 0.15 seconds is required to reach the operation of removing the micropore forming apparatus from the skin after the subject has felt the piercing).

It can be clearly understood from FIG. 19 that glucose transmittance is increased by pressing the microneedles on the skin after piercing. Double the glucose transmittance of the conventional method was obtained even at a bodily sensation pressing time of zero seconds, and understandably the transmittance increased in accordance with the extension of the pressing time. Note that the time during which the microneedles are pressed on the skin after piercing is preferably less than 60 seconds when considering the burden on the subject and reducing the measurement time. However, the specific time of pressing the microneedles on the skin after piercing is preferably 0.15 seconds or longer when considering substantially increasing the transmittance even at bodily sensation zero seconds (actually pressing for approximately 0.15 seconds).

Figure 20:
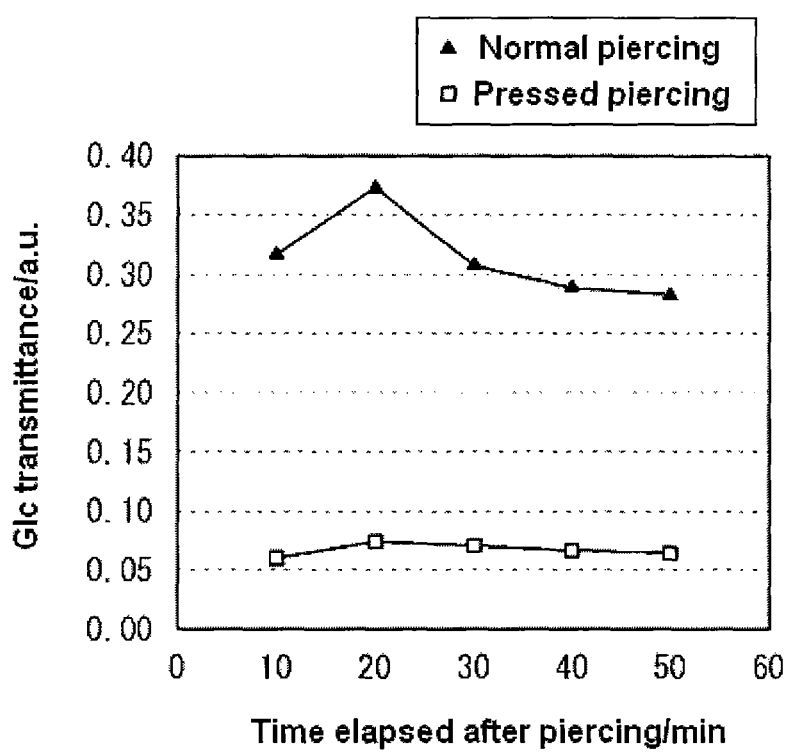
FIG. 20 shows the relationship between the length of the time after piercing and the glucose transmittance.

FIG. 20 shows the confirmed results transition of glucose transmittance according to elapsed time after piercing by the conventional method (normal piercing) and the method of the present invention (pressed piercing). The microneedle speed when striking the epidermal layer during pressed piercing was 5 (m/s), and the pressing time after piercing was 1 minute. The microneedle speed when striking the epidermal layer during normal piercing was 6 (m/s). The extraction surface area was 5×10 mm², and 90 μL of RO water was used as the extraction medium. It can be clearly understood from FIG. 20 that the method of the present invention, in which the microneedles were pressed on the skin after piercing, produced approximately 5 times the transmittance over the time course compared to forming micropores using a conventional piercing device.

[Transmittance and Damage]

From the perspective of improving accuracy, forming as many micropores as possible in the skin of the subject is preferable; however, when considering the burden on the subject, it is preferable to reduce damage such as hemorrhage and pain associated with piercing.

Figure 21:
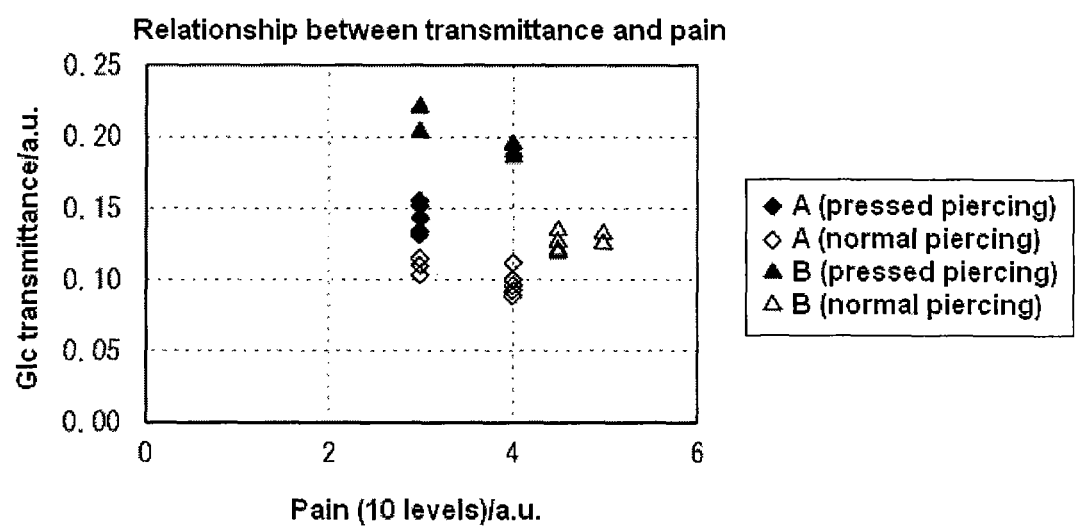
FIG. 21 shows the relationship between glucose transmittance and pain.
Figure 22:
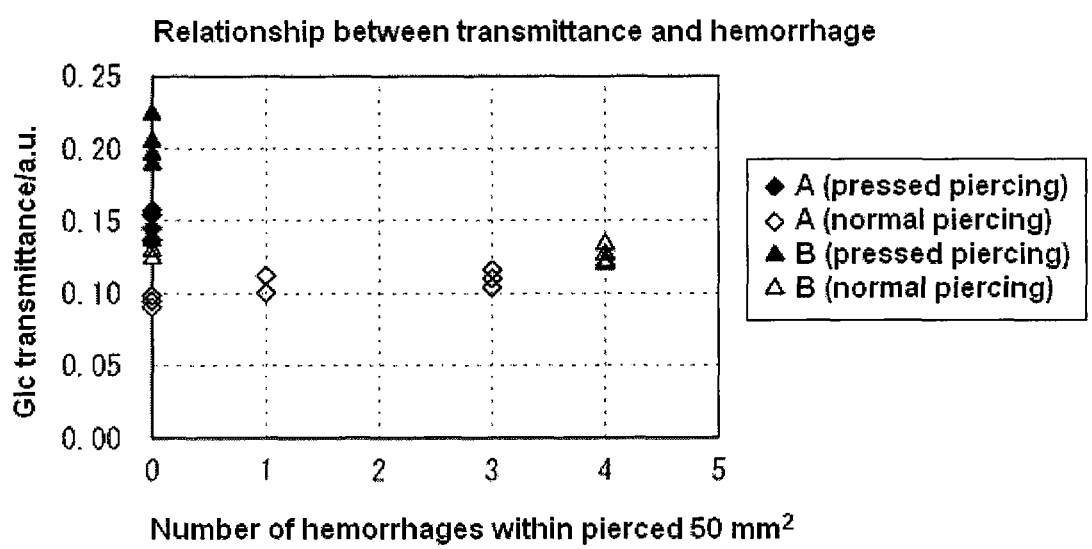
FIG. 22 shows the relationship between glucose transmittance and hemorrhage.

Two subjects, subject A and subject B, were used in piercing tests under the following conditions, and the relationship between glucose transmittance and damage to the subject was verified. The results are shown in FIGS. 21 and 22.

[Test Conditions]

*Piercing: Piercing while pressing according to the present invention and normal piercing (comparative example).

The microneedle speed when striking the epidermal layer during pressed piercing was 5 (m/s), and the pressing time after piercing was the bodily sensation zero seconds. The microneedle speed when striking the epidermal layer during normal piercing was 8.5 (m/s).

*Number of Body areas: pressed piercing in 2 areas, and normal piercing in 3 areas.

*Extraction Conditions:
Extraction area: 5×10 mm²
Extraction Time: 10 minutes performed 3 times=30 minutes
Extraction Medium/Amount: RO water/90 μL

*Evaluation Items:
Transmittance: glucose (Glc) transmittance was measured
Damage: Pain, hemorrhage FIG. 21 shows the relationship between glucose transmittance and pain. Subject pain was subjectively evaluated in 10 relative levels. It can be understood from FIG. 21 that pain by pressed piercing was equal to or less than that by normal piercing, and glucose transmittance was high. FIG. 22 shows the relationship between glucose transmittance and hemorrhage. Although hemorrhage may occur from micropores formed by piercing, the number of such locations were visually counted by the number of small hemorrhagic red dots observed in the microneedle area of the microneedle array. It can be understood from FIG. 22 that although no hemorrhages were observed by pressed piercing, the glucose transmittance was greater than that by normal piercing.

[Pressing Force and Damage]

An aspect of the present invention is pressing the microneedles toward the skin after piercing, and whether the force exerted in pressing the microneedles toward the skin influenced pain and hemorrhage was investigated. The pressing pressure (pa) of the microneedles toward the skin was changed by changing the compression distance (mm) of the discharge spring exerting a force on the microneedles on the skin. The pressing force toward the skin increased as the discharge spring compression distance increased. The results are shown in Tables 1 and 2. Table 1 shows the relationship between pain and pressing force, and Table 2 shows the relationship between hemorrhage and pressing force.

In Table 1, [Pressing Only] is defined as manually holding the microneedle tip under a state of force exerted by the discharge spring, with the microneedles of the microneedle tip contacting the specimen skin at low speed (0.6 m/s), and the microneedles pressing the skin via the force exerted by the discharge spring. [Discharge and Pressing] is defined as moving the piston to the skin side by releasing the stopper in the loaded state shown in FIG. 18(*b*) so that the microneedles strike the skin, and pressing the microneedles on the skin via the force exerted by the discharge spring after piercing.

TABLE 1

| Discharge spring compression distance (mm) | Pressing Only | | Discharge and Pressing | |
|---|---|---|---|---|
| | Specimen 1 | Specimen 2 | Specimen 1 | Specimen 2 |
| 8 | No pain | No pain | No pain | No pain |
| 10 | No pain | No pain | No pain | No pain |
| 11 | No pain | No pain | Pain | Pain |

TABLE 2

| Discharge Spring Compression Distance (mm) | Pressing Only | | Discharge and Pressing | |
|---|---|---|---|---|
| | Specimen 1 | Specimen 2 | Specimen 1 | Specimen 2 |
| 8 | No Hemorrhage | No Hemorrhage | No Hemorrhage | No Hemorrhage |
| 10 | No Hemorrhage | No Hemorrhage | No Hemorrhage | No Hemorrhage |
| 11 | No Hemorrhage | No Hemorrhage | No Hemorrhage | No Hemorrhage |

According to Table 1, there was no change in the evaluation of [Pressing Only] as [No Pain] even when the pressing force was increased by increasing the compression distance of the discharge spring to 8 mm, 10 mm, and 11 mm. The only cases resulting in [Pain] for [Discharge and Pressing] were at discharge spring compression distance of 11 mm. Thus, the subject's sensation of pain is influenced by the striking speed (piercing speed) of the microneedles on the skin, whereas pressing the microneedles on the skin after piercing does not result in pain.

According to Table 2, there was no hemorrhage for either [Pressing Only] or [Discharge and Pressing] even when the discharge spring compression distance was increased to 8 mm, 10 mm, and 11 mm, and neither did pressing force affect hemorrhage.

The micropore forming method of the present invention presses the microneedles on the skin for a predetermined time after the microneedles have pierced the skin, and a force is exerted by the discharge spring so that the microneedles are not withdrawn from the skin after piercing. When the exerted force is increased so as to have excessive striking speed on the skin surface, the subject experiences pain. Therefore, the speed of the microneedles striking the skin surface and the force exerted on the microneedles on the skin should be in a preferred range. This range will differ depending on microneedle specifications (shape, number, material and the like), and examples are described below based on Table 3.

TABLE 3

| Discharge Spring Compression Distance [mm] | Pressing force [Pa] | microneedle Behavior | Piercing Speed [m/s] | Pain | Hemorrhage |
|---|---|---|---|---|---|
| 2.5 | 1667 | microneedle Withdrawal From Skin After Piercing | 4 | No pain | No Hemorrhage |
| 5 | 140000 | microneedle Withdrawal From Skin After Piercing | 4.6 | No pain | No Hemorrhage |
| 6 | 212000 | microneedle Withdrawal From Skin After Piercing | 4.7 | No pain | No Hemorrhage |
| 7 | 256000 | microneedle Not Withdrawn from Skin After Piercing | 4.8 | No pain | No Hemorrhage |
| 8 | 306000 | microneedle Not Withdrawn from Skin After Piercing | 4.9 | No pain | No Hemorrhage |
| 10 | 416667 | microneedle Not Withdrawn from Skin After Piercing | 6.1 | No pain | No Hemorrhage |
| 11 | 472000 | microneedle Not Withdrawn from Skin After Piercing | 6.7 | Pain | No Hemorrhage |

The microneedles of Table 3 were 305 microneedles made of synthetic resin covering a rectangular region (5×10 mm) as shown in FIGS. 11 and 12. The microneedles were conical and the apex angle was 30 degrees. The discharge spring compression distance was changed by changing the size of the spacer (refer to FIG. 18 in contact with one end (the opposite end from that on the subject skin side) of the discharge spring. The behavior of the microneedles (whether withdrawn from the skin after piercing) and presence of pain and hemorrhage were evaluated.

In the examples shown in Table 3, the microneedles were withdrawn from the skin after piercing when the piercing speed was 4.7 m/s, and the microneedles were not withdrawn from the skin after piercing when the piercing speed was 4.8 m/s. It is therefore preferable that the microneedles strike the skin at a speed of 4.8 m/s or more. However, the subject experienced pain when the piercing speed was 6.7 m/s, and the subject did not feel pain when the piercing speed was 6.1 m/s. Therefore, it is preferable that the speed at which the microneedles strike the skin is 6.1 m/s or less.

The microneedles were withdrawn from the skin after striking when the pressing force was $2.12 \times 10^{-5}$ (Pa), but the microneedles were not withdrawn from the skin after striking the skin when the pressing force was $2.56 \times 10^{-5}$ (Pa). Therefore the microneedle pressing force is preferably $2.56 \times 10^5$ (Pa) or more.

[Modifications]

Note that the present invention is not limited to the previously described embodiment and may be variously modified. For example, the shape of the members configuring the chuck array, that is, the skin contact part, and the method of installing the main spring, that is, the force exerting means, may be variously modified.

Although 305 conical microneedles are arranged in a rectangular region as the microneedle tip in the above embodiment, the number, shape and material of the microneedles as well as the shape of the microneedle tip provided with these microneedles may be variously modified.

Although only a main spring for exerting a force on the chuck array in the piercing direction is used as the means for exerting a force on the chuck array in the above embodiment, a pressing spring that has a small spring constant may be disposed in the guide channel of the rear cover and in the guide channel of the front cover to prevent the leading end of the microneedles from protruding outside from the opening of the tip receiver installation member when the micropore forming apparatus is removed from the skin of the subject after piercing and after completion of the pressing operation. In this case, the specifications of the length and spring constant of the main spring must be selected so as to provide a force to press the microneedles on the skin when the guide part has compressed the pushing spring and the microneedles have struck the skin.

The micropore forming apparatus also may be provided with a timer to alert the subject to the length of time the microneedles have been pressed on the skin. In this case, a timer power source can be turned ON by the operation of installing the microneedle tip in the chuck array and moving the chuck array to the discharge position, and the timer can be started by the discharge of the chuck array.

What is claimed is:

1. A micropore forming apparatus for forming micropores in the skin by piercing the skin of a subject with microneedles comprising:
   a skin contact part that has a plurality of microneedles for piercing the skin of the subject; and
   a spring for exerting a force on the skin contact part toward the skin of the subject;
   wherein the spring has a length so as to maintain the state of compression of the spring and thereby maintain the state of the microneedles being pressed into the skin after the microneedles have initially pierced the skin of the subject,
   wherein, after the microneedles have pierced the skin, the spring exerts a force P (Pa) on the skin through the microneedles such that $2.56 \times 10^5 \leq P$.

2. The micropore forming apparatus of claim 1, wherein the speed S (m/s) of the microneedles piercing the skin is set such that $4.8 \leq S$.

3. The micropore forming apparatus of claim 1, wherein the speed S (m/s) of the microneedles piercing the skin is set such that S is $\leq 6.1$.

4. A micropore forming method for forming micropores in the skin of a subject using a micropore forming apparatus for forming micropores in the skin by piercing the skin of the subject with microneedles;
   wherein the micropore forming apparatus comprises:
   a skin contact part that has a plurality of microneedles for piercing the skin of the subject; and
   a spring for exerting a force on the skin contact part toward the skin of the subject;
   wherein the spring has a length so as to maintain the state of compression of the spring and thereby maintain the state of the microneedles being pressed into the skin after the microneedles have initially pierced the skin of the subject,
   the method further comprising collecting interstitial fluid extracted from the micropores by an extraction medium.

5. The micropore forming method of claim 4, wherein the predetermined time is 0.15 second or longer.

6. The micropore forming method of claim 5, wherein the predetermined time is 60 seconds or less.

7. The micropore forming method of claim 4, wherein the speed S (m/s) of the microneedles piercing the skin is set such that $4.8 \leq S$.

8. The micropore forming method of claim 4, wherein the speed S (m/s) of the microneedles piercing the skin is set such that $S \leq 6.1$.

9. The micropore forming method of claim 4, wherein, after the microneedles have pierced the skin, the spring exerts a force P (Pa) on the skin through the microneedles such that $2.56 \times 10^5 \leq P$.

\* \* \* \* \*